United States Patent
Kühne

(10) Patent No.: US 12,099,115 B2
(45) Date of Patent: Sep. 24, 2024

(54) METHOD FOR OPERATING ELECTRONIC DATA GLASSES IN A MOTOR VEHICLE, AND ELECTRONIC DATA GLASSES

(71) Applicant: AUDI AG, Ingolstadt (DE)

(72) Inventor: Marcus Kühne, Beilngries (DE)

(73) Assignee: AUDI AG, Ingolstadt (DE)

( * ) Notice: Subject to any disclaimer, the term of this patent is extended or adjusted under 35 U.S.C. 154(b) by 816 days.

(21) Appl. No.: 17/051,648

(22) PCT Filed: Sep. 7, 2018

(86) PCT No.: PCT/EP2018/074169
§ 371 (c)(1),
(2) Date: Oct. 29, 2020

(87) PCT Pub. No.: WO2019/210984
PCT Pub. Date: Nov. 7, 2019

(65) Prior Publication Data
US 2021/0231796 A1   Jul. 29, 2021

(30) Foreign Application Priority Data
Apr. 30, 2018   (DE) .................. 10 2018 206 658.2

(51) Int. Cl.
*G01S 13/931* (2020.01)
*G02B 27/01* (2006.01)
*G06F 1/16* (2006.01)

(52) U.S. Cl.
CPC ........ *G01S 13/931* (2013.01); *G02B 27/0172* (2013.01); *G06F 1/163* (2013.01); *G01S 2013/9322* (2020.01)

(58) Field of Classification Search
CPC .......... G02B 27/017; G02B 2027/0178; G02B 2027/014; G02B 27/0093; G02B 27/01;
(Continued)

(56) References Cited

U.S. PATENT DOCUMENTS 8,690,750 B2 * 4/2014 Krueger ................ A61M 21/00
600/27
11,092,695 B2 * 8/2021 Song ..................... G01S 19/396
(Continued)

FOREIGN PATENT DOCUMENTS

DE    20116469 U1 * 1/2002 ............. B60N 3/00
DE    10156219 C1 * 8/2003 ............. A61B 5/18
(Continued)

OTHER PUBLICATIONS

DE102017006231A1 (Year: 2018).*
(Continued)

*Primary Examiner* — Olumide Ajibade Akonai
(74) *Attorney, Agent, or Firm* — STAAS & HALSEY LLP

(57) ABSTRACT

Contents are displayed by use of electronic smartglasses a vehicle occupant is wearing in a motor vehicle. The electronic smartglasses have a satellite-based capturing device by use of which a position of the motor vehicle is continuously captured. A movement of the motor vehicle is ascertained based on the continuously captured position of the motor vehicle and the contents displayed by use of the electronic smartglasses are adapted to the ascertained movement of the motor vehicle to prevent kinetosis in the vehicle occupant.

12 Claims, 1 Drawing Sheet

(58) Field of Classification Search
CPC .... G02B 2027/0185; G02B 2027/0127; G02B 27/0179; G02B 2027/0183; G02B 2027/0118; G02B 27/0172; G06F 3/011; G06F 1/163; G06F 3/012; G06F 3/013; G06F 3/0346; B60K 2370/1529; G06V 20/20; H04N 2007/145; A61M 21/00; A61M 2021/0022; A61M 2230/63; A61M 2205/507; G06T 2215/16; G06T 2219/2016; G01S 13/931; G01S 2013/9322; G16H 40/63

See application file for complete search history.

(56) References Cited

U.S. PATENT DOCUMENTS

| | | | |
|---|---|---|---|
| 2007/0034212 | A1 | 2/2007 | Brendley et al. |
| 2014/0025225 | A1* | 1/2014 | Armitage ............... B60W 40/09 701/1 |
| 2014/0176296 | A1 | 6/2014 | Morgan |
| 2017/0139473 | A1 | 5/2017 | Alaniz et al. |
| 2018/0040163 | A1* | 2/2018 | Donnelly ................ G06F 3/011 |
| 2018/0095280 | A1 | 4/2018 | Gallery et al. |
| 2019/0110016 | A1* | 4/2019 | Hurd ......................... G06T 7/32 |
| 2019/0130878 | A1* | 5/2019 | Bradley ................ B60W 50/14 |
| 2019/0317328 | A1* | 10/2019 | Bae .................... G02B 27/0093 |

FOREIGN PATENT DOCUMENTS

| | | |
|---|---|---|
| DE | 20 2014 005 329 U1 | 12/2014 |
| DE | 10 2014 220 053 A1 | 7/2015 |
| DE | 10 2014 015 871 A1 | 4/2016 |
| DE | 10 2014 221 608 A1 | 4/2016 |
| DE | 10 2014 019 579 A1 | 6/2016 |
| DE | 10 2015 207 337 A1 | 10/2016 |
| DE | 102017006231 A1 * | 1/2018 |
| DE | 10 2017 005 982 A1 | 2/2018 |
| DE | 10 2018 206 658.2 | 4/2018 |
| WO | WO-2016188545 A1 * | 12/2016 |
| WO | WO-2018007003 A1 * | 1/2018 |
| WO | PCT/EP2018/074169 | 9/2018 |

OTHER PUBLICATIONS

International Search Report (Forms PCT/ISA/210, PCT/ISA/220) dated Jan. 23, 2019, in International Patent Application No. PCT/EP2018/074169.

Written Opinion of the International Searching Authority dated Jan. 23, 2019, in International Patent Application No. PCT/EP2018/074169.

Examination Report dated Jan. 9, 2019, in German Patent Application No. 10 2018 206 658.2.

International Preliminary Report on Patentability dated Nov. 12, 2020, in International Patent Application No. PCT/EP2018/074169, including English language translation of Written Opinion (15 pages total).

Examination Report dated Jan. 8, 2024, in European Patent Application No. 18 773 356.3.

Chinese Office Action dated Sep. 22, 2023 for parallel Chinese Patent Application No. 201880092815.3.

German Office Action dated Mar. 4, 2024 for German Application No. 10 2018 206 658.2.

* cited by examiner

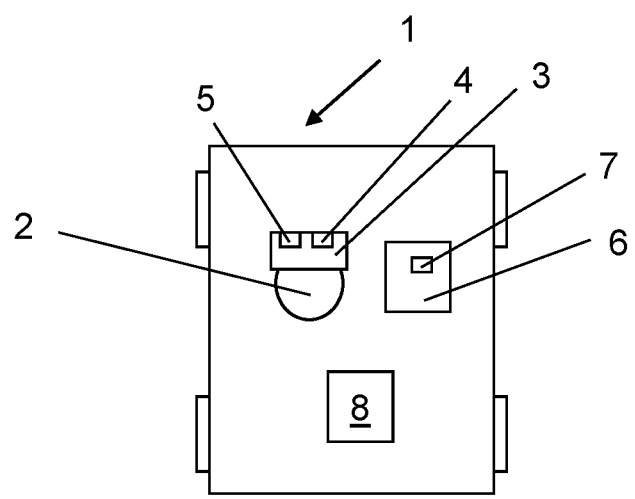

METHOD FOR OPERATING ELECTRONIC DATA GLASSES IN A MOTOR VEHICLE, AND ELECTRONIC DATA GLASSES

CROSS REFERENCE TO RELATED APPLICATIONS

This application is a U.S. national stage of International Application No. PCT/EP2018/074169, filed on Sep. 7, 2018. The International Application claims the priority benefit of German Application No. 10 2018 206 658.2 filed on Apr. 30, 2018. Both the International Application and the German Application are incorporated by reference herein in their entirety.

BACKGROUND

Described herein is a method for operating electronic smartglasses in a motor vehicle. Also described herein is an electronic smartglasses for displaying contents.

The use of electronic smartglasses, such as augmented reality glasses or virtual reality glasses, in motor vehicles is already known per se. For example, it is possible by use of such electronic smartglasses for vehicle occupants to watch movies, play computer games, or to have additional information relating to real objects in their environment be displayed.

When vehicle occupants use such electronic smartglasses during driving operation, it is possible that they develop kinetosis, or what is known as simulator sickness. Kinetosis is also referred to as travel or motion sickness. Symptoms can include physical reactions such as paleness, dizziness, headache, nausea, and vomiting. According to the prevailing opinion, kinetosis develops when the sensory organs provide contradictory information relating to the spatial orientation and movement of the body. This can happen when electronic smartglasses are used in motor vehicles. Depending on what the electronic smartglasses display at that moment, the eyes of the wearer of the electronic smartglasses can provide sensory impressions that contradict the sensory impressions of the equilibrium organ because the motor vehicle might move differently than is visually perceived by the wearer of the electronic smartglasses on account of the displayed contents.

German Patent Application No. 20 2014 005 329 U1 relates to the problem that a vehicle occupant could sometimes develop nausea while wearing electronic smartglasses. It is proposed to use a contactless, optical or acoustic sensor for position capturing and movement tracking of the smartglasses, which sensor cooperates with an automatic closed-loop or open-loop control system of the smartglasses.

German Patent Application No. 10 2014 221 608 A1 describes a method for deactivating a contact-analog display on smartglasses depending on the movement of a vehicle. A contact-analog display on the smartglasses is interrupted as long as the vehicle movement exceeds a threshold value.

German Patent Application No. 10 2014 015 871 A1 describes a display system for a motor vehicle, wherein the display system includes virtual reality glasses. Provision is made in that case to use a capturing device that is already present in the motor vehicle and is embodied for capturing the position and gestures of a vehicle occupant additionally also for capturing a position of the virtual reality glasses within the motor vehicle.

SUMMARY

Described herein is a solution by which it is possible to reliably and easily prevent kinetosis in a vehicle occupant wearing electronic smartglasses.

This is achieved by a method for operating electronic smartglasses in a motor vehicle and by electronic smartglasses having features as described herein. Advantageous configurations with practical and nontrivial developments are further described herein.

In the method described herein for operating electronic smartglasses in a motor vehicle, contents are displayed by use of the electronic smartglasses that a vehicle occupant is wearing. The electronic smartglasses have a satellite-based capturing device by use of which a position of the motor vehicle is continuously captured. A movement of the motor vehicle is ascertained based on the continuously captured position of the motor vehicle. The contents displayed by use of the electronic smartglasses are adapted to the ascertained movement of the motor vehicle in order to prevent kinetosis in the vehicle occupant.

The satellite-based capturing device of the electronic smartglasses can be, for example, a GPS sensor. However, other sensors which enable satellite-based position capturing of the motor vehicle and thus also of the electronic smartglasses are likewise possible. In the method described herein it is easily possible to continuously ascertain the position of the motor vehicle and thus also the movement of the motor vehicle solely by use of the electronic smartglasses. It is thus possible to prevent kinetosis in the vehicle occupant wearing the electronic smartglasses by adapting the contents displayed by use of the electronic smartglasses to the ascertained movement of the motor vehicle.

Data that characterize the absolute movement of the motor vehicle and thus the absolute movement of the electronic smartglasses are thus always available to the electronic smartglasses. Aspects of the disclosure are based on the finding that, when people in a vehicle wish to use in particular virtual reality or augmented reality contents without developing problems related to kinetosis or simulator sickness, it is necessary to reconcile the contents displayed by use of the electronic smartglasses partially or entirely with the absolute movements of the wearer of the electronic smartglasses.

The absolute movement of the vehicle occupant is reliably ascertained in the method described herein by virtue of the satellite-based capturing device that is integrated in the electronic smartglasses continuously capturing the positions of the motor vehicle. When the position of the motor vehicle or the continuous change in position of the motor vehicle is known, it is possible to continuously ascertain movements of the motor vehicle while the electronic smartglasses display contents. By reconciling the contents displayed by use of the electronic smartglasses partially or entirely with the movements of the motor vehicle, kinetosis in the vehicle occupant can be reliably prevented. It is thus possible by way of the method described herein to ensure that the vehicle occupant develops no contradictory sensory impressions in which the perceived motion of the motor vehicle and the perceived displayed contents do not match.

According to one advantageous embodiment described herein, the electronic smartglasses have a sensor device by use of which movements of the smartglasses are captured, wherein the contents displayed by use of the electronic smartglasses are additionally adapted to the captured movements of the smartglasses to prevent kinetosis in the vehicle occupant. The sensor device may for example be acceleration sensors. However, other sensors are likewise possible, provided reliable movement capturing of the smartglasses is possible. The smartglasses can thus capture their own movements by use of the sensor device that is integrated therein. The contents displayed by use of the electronic smartglasses are adapted to the captured movements of the smartglasses in order to prevent kinetosis in the vehicle occupant. In addition to the pure vehicle movement, head movements of the wearer of the electronic smartglasses can also in this way be captured and taken into account when controlling the smartglasses for displaying the contents. It is thus particularly reliably possible to resolve contradictory optical sensory impressions and sensory impressions of the equilibrium organ of the wearer of the electronic smartglasses to prevent kinetosis. In this case, too, the electronic smartglasses alone are able to generate or collect all the data that are necessary to prevent kinetosis.

A further advantageous embodiment described herein makes provision that a position of the motor vehicle is continuously captured by use of a mobile device that is arranged in the motor vehicle and has a satellite-based capturing device and, based thereon, a movement of the motor vehicle is likewise ascertained and, to prevent kinetosis in the vehicle occupant, the contents displayed by use of the electronic smartglasses are adapted to the movement of the vehicle ascertained by use of the mobile device. The mobile device is for example a smartphone, which transfers data characterizing the ascertained movement of the motor vehicle to the electronic smartglasses, for example wirelessly. It is thus additionally also possible using the mobile device to continuously ascertain the position of the motor vehicle and thus the movement of the motor vehicle in order to prevent kinetosis by correspondingly controlling the smartglasses. In particular if the mobile device is a smartphone, it is already usually carried by the vehicle occupant. It is thus also possible, for example, to compare the data provided with respect to the vehicle movement or position change of the motor vehicle of the mobile device and of the electronic smartglasses. It is thus possible to generate particularly exact movement data of the vehicle. For example if the satellite-based capturing device of the electronic smartglasses malfunctions at some point, it is still possible for the mobile device to provide data for capturing the movement of the motor vehicle.

In a further advantageous configuration described herein, provision is made that data characterizing a movement of the motor vehicle are transmitted by use of the motor vehicle to the electronic smartglasses that adapts the contents displayed to the ascertained movement of the motor vehicle in order to prevent kinetosis of the vehicle occupant. For this purpose, the motor vehicle can for example have a wireless or indeed cable-bound interface via which the data characterizing the movement of the motor vehicle can be transmitted to the electronic smartglasses. It is thus possible to provide particularly exact movement data of the motor vehicle because data characterizing the movement of the motor vehicle are provided by the motor vehicle itself. In modern motor vehicles, typically a multiplicity of sensors are integrated by use of which accelerations and velocities are permanently captured. These data can be provided for example via a BUS system through the use of the interface of the electronic smartglasses. It is thus possible to prevent kinetosis in a particularly reliable manner.

The electronic smartglasses described herein for displaying contents, includes a satellite-based capturing device for continuously capturing a position of a motor vehicle, wherein the electronic smartglasses are configured to ascertain a movement of the motor vehicle based on the continuously captured position of the motor vehicle and to adapt the displayed contents to the ascertained movement of the motor vehicle to prevent kinetosis in a vehicle occupant wearing the electronic smartglasses. Advantageous configurations of the method described herein should be regarded as advantageous configurations of the electronic smartglasses described herein and vice versa, wherein the electronic smartglasses for example have components for performing the method operations.

An advantageous embodiment of the electronic smartglasses makes provision that the satellite-based capturing device is a GPS sensor. However, other sensors for satellite-based position capturing can likewise be integrated in the electronic smartglasses.

The electronic smartglasses are for example virtual reality glasses or augmented reality glasses. It is furthermore also possible that the electronic smartglasses are mixed reality glasses.

Further advantages, features, and details emerge from the description of the example embodiments below and based on the single drawing. The features and feature combinations stated in the description above and the features and feature combinations illustrated below in the description of the drawing and/or in the drawing alone are not only usable in the combination that is stated in each case but also in other combinations or alone, without departing from the scope of the disclosure.

BRIEF DESCRIPTION OF THE DRAWINGS

These and other aspects and advantages will become more apparent and more readily appreciated from the following description of the example embodiments, taken in conjunction with the accompanying single drawing which is a schematic illustration of a motor vehicle, in which a vehicle occupant wearing electronic smartglasses is seated.

DETAILED DESCRIPTION

Reference will now be made in detail to examples which are illustrated in the accompanying drawing, wherein like reference numerals refer to like elements throughout.

A motor vehicle 1 is shown in a highly schematic illustration in the only drawing. A vehicle occupant 2 wearing electronic smartglasses 3 is seated in the motor vehicle 1. The electronic smartglasses 3 may, for example, be virtual reality glasses or augmented reality glasses. The electronic smartglasses 3 serve for displaying a variety of contents and includes a satellite-based capturing device 4 for continuously capturing a position of the motor vehicle 1. The electronic smartglasses 3 are set up to ascertain, based on the continuously captured position of the motor vehicle 1, a movement of the motor vehicle 1 and to adapt the contents displayed by use of the electronic smartglasses 3 to the ascertained movement of the motor vehicle 1 in order to prevent kinetosis in the vehicle occupant 2.

If, for example, a movie is shown by use of the electronic smartglasses 3 while traveling with the motor vehicle 1, provision may be made that symbols or other movements that correspond to the captured movement of the motor vehicle 1 are displayed for example in a peripheral region. The movie can then be shown in a central and for example larger display region.

For example, it is also possible that a computer game played by the vehicle occupant 2 while traveling with the motor vehicle 1 is shown by use of the electronic smartglasses 3. In this context, for example, provision may be made that the virtual movement of the vehicle occupant 2 within the computer game shown corresponds to the captured movement of the motor vehicle 1. It is possible to ensure in this way that no contradictory sensory impressions arise in the vehicle occupant 2. This is because the movement due to the movement of the motor vehicle 1 that is actually perceived by the vehicle occupant 2 and the visual perception of the displayed contents shown by use of the electronic smartglasses 3 at least substantially match as a result.

The contents displayed by use of the electronic smartglasses 3 are thus partially or entirely made consistent with the captured movements of the motor vehicle 1. In this way, the occurrence of simulator sickness or kinetosis in the vehicle occupant 2 can be prevented or at least reduced to a significant extent.

The electronic smartglasses 3 additionally include a sensor device 5 by use of which movements of the smartglasses 3 are captured. The contents displayed by use of the electronic smartglasses 3 are additionally adapted to the captured movements of the smartglasses 3 in order to prevent kinetosis in the vehicle occupant 2. The sensor device 5 can be, for example, one or more acceleration sensors by use of which movements of the smartglasses 3 can be continuously captured.

In addition, a mobile device 6 in the form of a smartphone, having a satellite-based capturing device 7, is additionally arranged in the motor vehicle 1. A position of the motor vehicle 1 is continuously captured by use of the satellite-based capturing device 7 and, based thereon, movements of the motor vehicle 1 are likewise ascertained. The contents displayed by use of the electronic smartglasses 3 are adapted to the movement of the motor vehicle 1 ascertained by use of the mobile device 6 to prevent kinetosis in the vehicle occupant 2. It is thus redundantly possible to capture the position change and movement of the motor vehicle 1 both by use of the electronic smartglasses 3 and by use of the mobile device 6 in order to prevent kinetosis in the vehicle occupant 2 in the manner already described. If one of the satellite-based capturing devices 4, 7 should malfunction, it is possible to furthermore reliably ensure that the position change and thus also movements of the motor vehicle 1 can continue to be captured to correspondingly control the electronic smartglasses 3 with knowledge of the data to prevent kinetosis.

It is additionally possible that data characterizing a movement of the motor vehicle 1 are transmitted by use of the motor vehicle 1 itself to the electronic smartglasses 3, which adapts the displayed contents to the ascertained movement of the motor vehicle to prevent kinetosis in the vehicle occupant 2. For this purpose, the motor vehicle 1 can have an interface 8 that is indicated here only schematically and is set up to transmit the data characterizing the movement of the motor vehicle 1, for example wirelessly to the electronic smartglasses 3. To this end, the motor vehicle 1 for example has a multiplicity of sensors by use of which accelerations and velocities of the motor vehicle 1 can be captured. The sensors can be connected to the interface 8 for example via a data BUS to transmit the data characterizing the movement of the motor vehicle 1 to the electronic smartglasses 3. The motor vehicle 1 itself can provide movement data in a particularly exact manner, with the result that kinetosis in the vehicle occupant 2 can be prevented particularly reliably using the data.

A description has been provided with reference to various examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV,* 358 F3d 870, 69 USPQ2d 1865 (Fed. Cir. 2004).

The invention claimed is:

1. A method for operating electronic smartglasses in a motor vehicle, in which contents are displayed by the electronic smartglasses a vehicle occupant is wearing, the method comprising:

continuously capturing, by a satellite-based capturing device included in the electronic smartglasses, a position of the motor vehicle;

continuously capturing, by a satellite-based capturing device included in a mobile device arranged in the motor vehicle, a position of the motor vehicle;

ascertaining a movement of the motor vehicle based on the position of the motor vehicle continuously and redundantly captured by the satellite-based capturing device included in the electronic smartglasses and the satellite-based capturing device included in the mobile device, the position of the motor vehicle continuously captured by the satellite-based capturing device included in the electronic smartglasses when the satellite-based capturing device included in the mobile device arranged in the motor vehicle has malfunctioned, and the position of the motor vehicle continuously captured by the satellite-based capturing device included in the mobile device when the satellite-based capturing device included in the electronic smartglasses has malfunctioned; and adapting the contents displayed by the electronic smartglasses based on the ascertained movement of the motor vehicle to prevent kinetosis in the vehicle occupant.

2. The method according to claim 1, further comprising capturing, by a sensor device included in the electronic smartglasses, movements of the electronic smartglasses, wherein adapting the contents displayed by the electronic smartglasses is further based on the movements of the electronic smartglasses captured by the sensor device.

3. The method according to claim 1, wherein:

the adapting the contents displayed by the electronic smartglasses is further based on the movement of the motor vehicle ascertained based on the position of the motor vehicle continuously captured by the satellite-based capturing device included in the electronic smartglasses and on the position of the motor vehicle continuously captured by the satellite-based capturing device included in the mobile device.

4. The method according to claim 3, further comprising transmitting, by the mobile device, data to the electronic smartglasses, wherein the data characterizes the movement of the motor vehicle ascertained based on the position of the motor vehicle continuously captured by the satellite-based capturing device included in the mobile device, and the mobile device is a smartphone.

5. The method according to claim 1, further comprising transmitting data from the motor vehicle to the electronic smartglasses, wherein the data characterizes a movement of the motor vehicle ascertained by the motor vehicle, and adapting the contents displayed by the electronic smartglasses is further based on the movement of the motor vehicle ascertained by the motor vehicle.

6. Electronic smartglasses for displaying contents, comprising:
a satellite-based capturing device configured to continuously capture a position of a motor vehicle, wherein the electronic smartglasses are configured to:
ascertain a movement of the motor vehicle based on the position of the motor vehicle continuously captured by the satellite-based capturing device,
receive a movement of the motor vehicle ascertained based on a position of the motor vehicle continuously captured by a satellite-based capturing device included in a mobile device, and
adapt, to prevent kinetosis in a vehicle occupant wearing the electronic smartglasses, the contents displayed by the electronic smartglasses to
the ascertained movement of the motor vehicle and the received movement of the motor vehicle continuously and redundantly captured by the satellite-based capturing device included in the electronic smartglasses and the satellite-based capturing device included in the mobile device, respectively,
the ascertained movement of the motor vehicle based on the position of the motor vehicle continuously captured by the satellite-based capturing device included in the electronic smartglasses when the satellite-based capturing device included in the mobile device has malfunctioned, and
the received movement of the mobile vehicle ascertained based on the position of the motor vehicle continuously captured by the satellite-based capturing device included in the mobile device when the satellite-based capturing device included in the electronic smartglasses has malfunctioned.

7. The electronic smartglasses according to claim 6, wherein the satellite-based capturing device is a GPS sensor.

8. The electronic smartglasses according to claim 6, wherein the electronic smartglasses are virtual reality glasses.

9. The electronic smartglasses according to claim 6, wherein the electronic smartglasses are augmented reality glasses.

10. The electronic smartglasses according to claim 6, further comprising:
a sensor device configured to capture movements of the electronic smartglasses,
wherein
the electronic smartglasses are configured to adapt the contents displayed by the electronic smartglasses based on the movements of the electronic smartglasses captured by the sensor device.

11. The electronic smartglasses according to claim 6, wherein
the electronic smartglasses are configured to adapt the contents displayed by the electronic smartglasses based on the movement of the motor vehicle ascertained based on the position of the motor vehicle continuously captured by the satellite-based capturing device included in the electronic smartglasses and on the position of the motor vehicle continuously captured by the satellite-based capturing device included in the mobile device.

12. The electronic smartglasses according to claim 6, wherein
the electronic smartglasses are configured to receive a movement of the motor vehicle ascertained based on a position of the motor vehicle captured by the motor vehicle, and
the electronic smartglasses are configured to adapt the contents displayed by the electronic smartglasses based on the movement of the motor vehicle ascertained based on the position of the motor vehicle captured by the motor vehicle.

* * * * *